United States Patent [19]

Thorpe

[11] Patent Number: 5,338,542
[45] Date of Patent: Aug. 16, 1994

[54] DISULFIDE LINKED IMMUNOTOXINS WITH MOLECULAR GROUPINGS IN THE LINKER WHICH CAUSE STERIC HINDRANCE TO THE DISULFIDE LINKAGE

[75] Inventor: Philip E. Thorpe, London, England

[73] Assignee: ICRF (Patents) Limited, London, England

[21] Appl. No.: 716,762

[22] Filed: Jun. 19, 1991

Related U.S. Application Data

[60] Continuation of Ser. No. 446,666, Dec. 6, 1989, which is a division of Ser. No. 90,386, Aug. 27, 1987, Pat. No. 4,880,935, which is a continuation of Ser. No. 884,641, Jul. 11, 1986, abandoned.

[51] Int. Cl.$^5$ .................. A61K 39/44; C07K 17/02; C07K 15/28
[52] U.S. Cl. .................. 424/180.1; 424/179.1; 424/155.1; 424/154.1; 530/391.1; 530/391.3; 530/391.5; 530/391.7; 530/391.9; 530/404; 530/408
[58] Field of Search .................. 424/85.8, 85.91; 530/391.1, 391.3, 391.5, 391.7, 391.9, 404, 408

[56] References Cited

U.S. PATENT DOCUMENTS

| | | | |
|---|---|---|---|
| 4,149,003 | 4/1979 | Carlsson et al. | 546/261 |
| 4,340,535 | 7/1982 | Voisin et al. | |
| 4,368,149 | 1/1983 | Masuko et al. | |

OTHER PUBLICATIONS

Thorpe et al (1988) Cancer Res 48:6396–6404 (Nov. 15th issue).
Wawzynczak et al (1987) In *Immunoconjugates. Antibody Conjugates in Radioimaging and Therapy of Cancer*, (Vogel ed) N.Y., Oxford Univ. Press pp. 28–55.
Shen et al (1988) Int. J. Cancer 42:792–797.
Hertler et al (1989) Cancer Immunol. Immunother. 28:59–66.
Brusa et al (1992) Cancer Immunol. Immunother. 35:373–380.
Ghetie et al (1991) J. Immunol. Methods 142:223–230.
Thorpe et al (1985) JNCI 75(1):151–159.
BACR Poster Sheets Mar. 24, 1985.
Blair et al (1983) J. Immunol Methods 59:129–143.
Myers et al (1984) Blood 63:1178–1185.
Vitetta et al (1983) Science 219:644–650.
Thorpe et al., Chemical Abstracts, vol. 108, (11), abst. No. 87663p, Mar. 14, 1988.
Cancer Research 47, 5924–5931 (1987) Thorpe et al.

*Primary Examiner*—Kay K. Kim
*Attorney, Agent, or Firm*—Nixon & Vanderhye

[57] ABSTRACT

The efficacy of immunotoxins having an antibody that recognises a tumour associated antigen linked to a cytotoxin through a heterobifunctional agent of the disulphide type is improved by providing in the heterobifunctional agent a molecular grouping creating steric hindrance in relation to the disulphide link. This steric hindrance can be provided by a methyl substituted methylene group located in the heterobifunctional link adjacent to the disulphide bond.

9 Claims, 1 Drawing Sheet

REACTION SCHEME

REACTION SCHEME
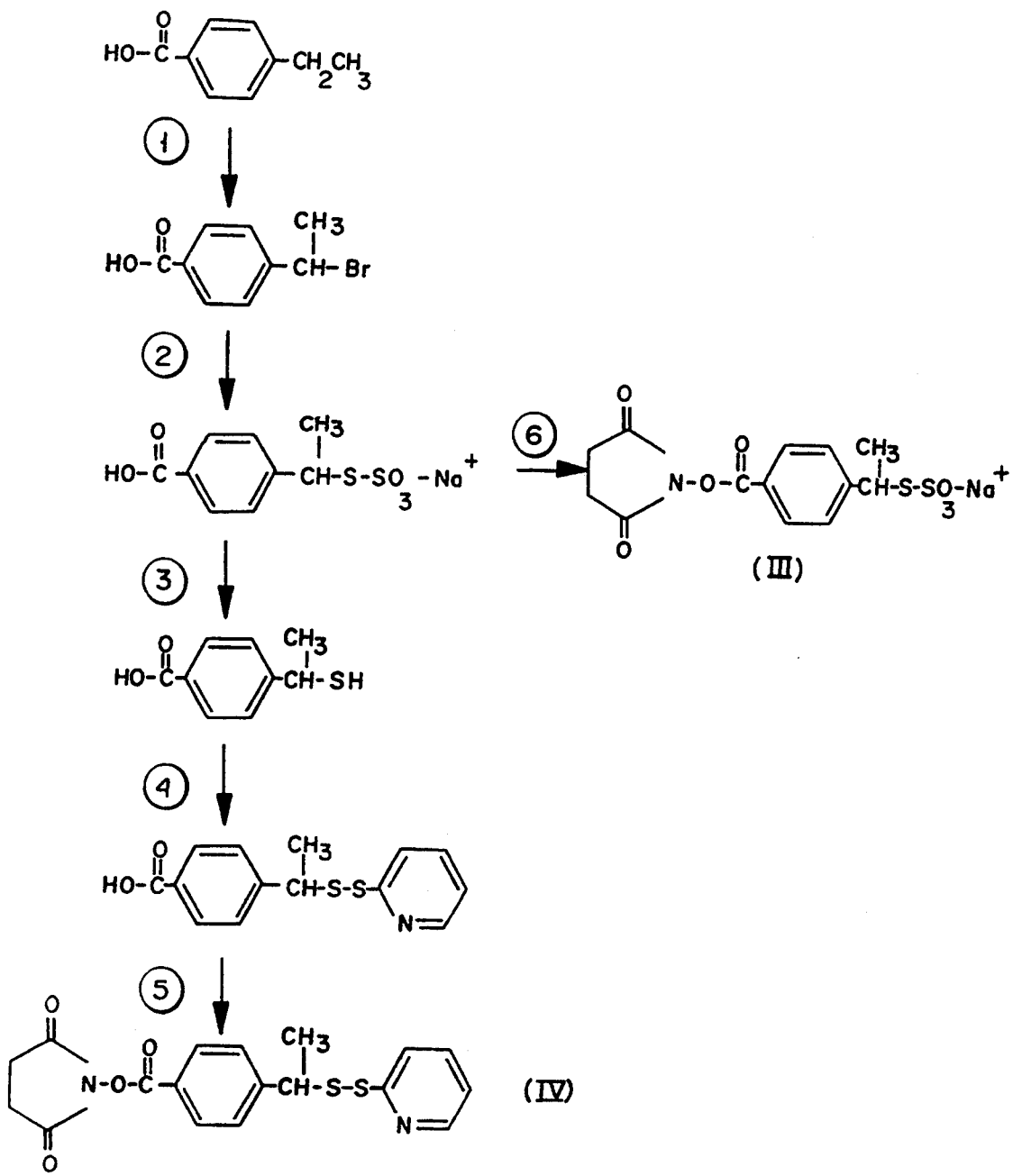

DISULFIDE LINKED IMMUNOTOXINS WITH MOLECULAR GROUPINGS IN THE LINKER WHICH CAUSE STERIC HINDRANCE TO THE DISULFIDE LINKAGE

This is a continuation of application Ser. No. 07/446,666, filed Dec. 6, 1989, which is a division of application Ser. No. 07/090,386, filed Aug. 27, 1987 now U.S. Pat. No. 4,880,935, which is a continuation of application Ser. No. 06/884/641, filed Jul. 11, 1986, now abandoned.

This invention relates to immunotoxins and is particularly concerned with the vision of immunotoxins of improved efficacy in vivo.

The use of immunotoxins in drug targeting is now well recognized. Such immunotoxins essentially comprise an antibody that recognises a tumour associated antigen that is linked to a suitable cytotoxin. The exact nature of the link is important in that it must provide a linkage between the antibody and the toxin that will remain intact during the delivery of the toxin through the patients body to the intended site of action and, at the same time, it must not interfere with the immunological specificity of the antibody or the cytotoxic properties of the toxin.

A group of linking agents known as heterobifunctional agents have been developed in recent years for this purpose. Two compounds that have achieved acceptability are N-succinimidyl-3-(2-pyridyldithio)propionate which has become known as SPDP and 2-iminothiolane hydrochloride which has become known as 2IT. These compounds, when used as heterobifunctional linking agents, produce immunotoxins of the structure

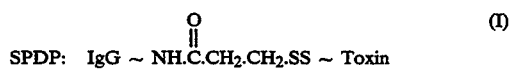

SPDP: IgG ~ NH.C.CH$_2$.CH$_2$.SS ~ Toxin    (I)

2IT: IgG ~ NH.C.CH$_2$.CH$_2$.CH$_2$.SS ~ Toxin    (II)

The disulphide bond appears to be necessary for cytotoxic activity, probably because the toxic component has to be released from the antibody by reduction inside the cell in order to inactivate the cells machinery for protein synthesis. The problem with such linking agents is that the essential disulphide bond is labile in the blood stream or extravascular tissues of mammals and experiments that have been carried out in mice indicate that there is degradation of the disulphide bond at a rate such that the immunotoxin has a half life of approximately 8 hours. This premature degradation of the immunotoxin is undesirable from the therapeutic point of view because the released antibody component from the immunotoxin is relatively stable in the mammal and can so mask the target antigen sites on the tumour from subsequently administered immunotoxin.

It has been found, in accordance with the present invention, that the rate of premature degradation of the immunotoxin can be reduced by structural modification of the heterobifunctional linking agent to provide a substituent masking or protecting the disulphide bond.

The present invention therefore provides an improved immunotoxin in which the heterobifunctional agent includes a molecular grouping that will create steric hindrance in relation to the disulphide link. Steric hindrance is most conveniently provided by a substituted methylene group adjacent to the disulphide link. The exact nature of the substituents is not of critical importance, the concept of the present invention being directed simply to the provision of bulky groups that will not interfere with the biological properties of the immunotoxin but which will afford a measure of shielding or protection to the disulphide link during the passage of the immunotoxin from the point of administration to the site of action. It will therefore be seen that the selection of the sterically hindering group is governed largely by considerations of biological inertness and ease of chemical synthesis and such considerations point to the use of one or more hydrocarbyl groups, e.g. containing from 1–6 carbon atoms, since they have been found to provide an adequate degree of protection to the disulphide link during its transport to the target cell but still permit cleavage of the disulphide bond in the target cell. Preferably, the molecular grouping contains both a substituted methylene group and a phenylene group adjacent to the disulphide link. The molecular grouping can have a carbon atom directly bonded to the disulphide group where the carbon atom is directly bonded to one or two $C_1$ to $C_4$ alkyl groups and also directly bonded to a benzene ring system. The molecular grouping can be —$C_6H_4$—CH(CH$_3$)—.

Our experiments indicate that a useful measure of protection of the disulphide group can be achieved by the incorporation of one methyl substituent onto a methylene group adjacent to the disulphide link. However, improved protection would be expected by the provision of larger substituents, e.g. 2 methyl groups or one or two $C_2$–$C_4$ alkyl groups which may be the same or different. From the practical point of view, one must balance the additional longevity of the immunotoxin in vivo against the additional difficulty and cost of synthesising the more sterically hindered heterobifunctional agents.

The improvement of the present invention is applicable to all heterobifunctional agents of the type which form a chemical bond with the antibody and which link with the toxin through the disulphide link. It is particularly suited to the modification of the existing heterobifunctional agents of the SPDP and 2IT type by the introduction of the selected steric hindering groups on the methylene adjacent to the disulphide group. For example, when SPDP is modified in accordance with the present invention, use may be made of linking agents having the formula

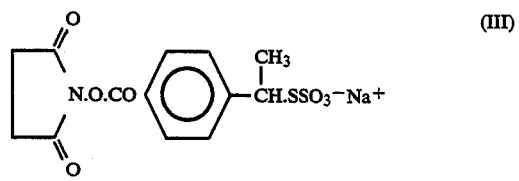

(III)

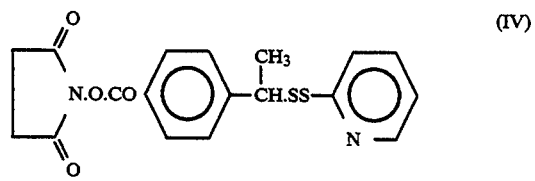

(IV)

In these compounds, it is preferred that X is methyl, Y is hydrogen and Z is sodium.

It is also possible to incorporate the concept of steric hindrance of the disulphide link in other heterobifunctional reagents, for example analogues of compounds III and IV above in which the succinimide ring is substituted by a sulphonic acid group and/or in which the pyridyl ring of SPDP is replaced by a 3-carboxy-4-nitrophenyl ring.

The antibody component of the immunotoxins of the invention may be any of the antibodies that recognise tumour associated antigens. The antibody will normally be a monoclonal antibody and will be selected in accordance with the nature of the tumor to be treated.

The cytotoxin component of the immunotoxins of the invention can again be any one of those cytotoxic materials customarily used in immunotoxins and in this connection, reference is made to Myers et al, Blood, 63, 1178–1185, (1984) and Thorpe et al, JNCI 75, 151–159 (1985). These papers describe the incorporation into immunotoxins of various ribosome inactivating proteins which are of particular interest in this invention. Typical ribosome inactivating proteins are the A chain of ricin and abrin. Other A chain like proteins which may be incorporated in the immunotoxins of this invention are bryodin, momordin, saporin, gelonin and PAP.

The immunotoxin of the present invention may be used in the same way as prior art immunotoxins to combat tumour growth in a host by administering an effective amount of the immunotoxin to the host. The immunotoxins are also particularly useful for purging bone marrow in vitro in connection with bone marrow transplantation. The purging can be carried out to remove leukaemic T. cells or other tumours in situations where bone marrow is removed from a patient and, after purging, replaced in the patient. Alternatively, it can be used to remove normal T. cells to reduce donor/host rejection in allograft situations where the patient receives donor bone marrow.

The following examples are given to illustrate the invention.

BRIEF DESCRIPTION OF THE DRAWING

The drawing sets forth the reaction scheme for producing a linker according to the invention.

EXAMPLE 1

Compounds III and IV are prepared as shown on the accompanying reaction scheme.

In step 1 p-ethyl benzoic acid is reacted with N-bromosuccinimide in carbon tetra-chloride in the presence of a benzoyl peroxide catalyst to introduce the alpha-bromo substituent.

In step 2 the bromo substituted compound prepared in step 1 is reacted with an excess of sodium thiosulphate in aqueous dioxan to give the thio-sulphite salt.

For the production of compound IV, the thio-sulphite is reacted in step 3 with a slight excess of dithiothreitol in water and the resulting thiol is then reacted in step 4 with a slight excess of bis-(2-pyridyl)disulphide in a 70% v/v dioxan/ethanol mixture. The resulting pyridyl disulphide is then reacted in step 5 with a slight molar excess of N-hydroxysuccinimide in the presence of an equivalent quantity of dicyclohexylcarbodimide in dimethyl formamide.

The resulting N-hydroxysuccinimide derivative can then be directly used for reaction with the antibody as described in Example 2 below when the hydroxysuccinimide ring will open and react at the amine group of a lysine residue in the antibody.

Alternatively, when it is desired to prepare compound III, the thiosulphite salt obtained after step 2 can be reacted with the slight molar excess of N-hydroxysuccinimide as described above to give compound III which again can be used directly, without further purification, for reaction at the amino group of the lysine residues of the antibody.

Higher analogues of compounds III and IV, having a larger substituent on the methylene adjacent to the disulphide link, can be obtained by analagous methods using the appropriately higher alkyl substituted benzoic acids as the starting material in step 1.

EXAMPLE 2

This example illustrates linking of a monoclonal antibody MRC-OX7 via linking agent IV to the A chain of ricin. OX7 is a mouse IgG$_1$ sub-class antibody produced from a hybridoma cell line MRC-OX7 which is described in Mason et al, Biochem.J.187, 1–20 (1980) and is available from the Medical Research Council Cellular Immunology Unit, University of Oxford, Oxford, England. OX7 recognises an antigen Thy 1.1 which is the antigen expressed by the lymphoma cell lines AKR-A and BW5147 which are obtainable respectively from Prof. I Maclennan of The Department of Experimental Pathology, Birmingham University, Birmingham, England and Dr. J. Hewitt of the Wellcome Research Laboratories, Beckenham, Kent, England.

1. To 22.5 mg of OX7 antibody at a concentration of 7.5 mg/ml in nitrogen-flushed borate-saline buffer (0.05 m borate, 0.3 m NaCl, pH 9.0) is added a four-fold molar excess of compound IV dissolved in dimethylformamide (0.02 ml reagent solution per ml of antibody solution).

2. After stirring at room temperature for 2 h, the solution is applied to a column (1.6 cm diameter×30 cm) of Sephadex G50 (M) equilibrated in phosphate-saline buffer (0.1M sodium phosphate, 0.1M NaCl, 1 mM diaminoethanetetraacetic acid, pH 7.5). The antibody/compound IV conjugate is collected in a volume of 10–12 ml and concentrated to about 3.5 ml by ultrafiltration using an Amicon YM2 membrane.

3. Ricin A-chain toxin (8 mg) is fully reduced by incubation for 1 h at room temperature in the presence of 50 mM dithiothreitol. It is then applied to the Sephadex G 25(F) column equilibrated with nitrogen-flushed phosphate-saline buffer. The A-chain fraction (about 15 ml) is added directly to the concentrated solution of antibody/compound IV conjugate prepared in 2 above.

4. The mixed solution is concentrated to about 5 ml by ultrafiltration and incubated at room temperature for 96 h. The resulting ricin A chain immunotoxin was then purified by gel filtration on a column of Sephacyl S 200.

EXAMPLE 3

The procedure described in Example 2 was repeated but using heterobifunctional agent III in place of reagent IV. The same immunotoxin is obtained.

The immunotoxin obtained in accordance with Example 2(4) or Example 3 was tested in mice by the procedure described in Thorpe et al, JNCI, 75, July 1985 151–159 at page 153. When the test is carried out as described in the paper using the immunotoxin prepared with SPDP and ricin A chain, the survival time of the animals was recorded and full details are given in Thorpe et al (supra). When this procedure was repeated replacing the OX7-SPDP-ricin A chain immunotoxin by the immunotoxin prepared in Example 2(4) above or Example 3, it was found that the medium survival time increased about 50%.

I claim:

1. In an immunotoxin comprising an antibody that recognizes a tumor associated antigen linked via a heterobifunctional agent of the disulphide type to a cytotoxin through a disulphide link, the improvement which comprises providing in the heterobifunctional agent a molecular grouping containing both a substituted methylene group and a phenylene group, the molecular grouping creating steric hinderance in relation to the disulphide link.

2. An immunotoxin according to claim 1 wherein the methylene group is substituted by one methyl group.

3. An immunotoxin according to claim 1 wherein the cytotoxin is the A chain of a cytotoxin having two chains linked to one another by a disulphide bridge.

4. An immunotoxin according to claim 3 wherein the cytotoxin is the A chain of ricin.

5. An immunotoxin according to claim 1 wherein the molecular grouping has a carbon atom directly bonded to the disulphide group, said carbon atom also being directly bonded to one or two $C_1$ to $C_4$ alkyl groups and also directly bonded to a benzene ring system.

6. An immunotoxin according to claim 1 wherein the molecular grouping is a $-C_6H_4-CH(CH_3)-$ group.

7. A process for making an immuotoxin by linking an antibody that recognizes a tumor associated antigen to a cytotoxin via a heterobifunctional agent of the disulphide type which comprises the heterobifunctional agent of claim 1.

8. A method of combatting tumor growth in a host which comprises administering an effective amount of an immunotoxin according to claim 1 to the host.

9. A method or purging bone marrow which comprises contacting the bone marrow with an immunotoxin according to claim 1.

* * * * *